United States Patent [19]
Schelten et al.

[11] Patent Number: 5,285,073
[45] Date of Patent: Feb. 8, 1994

[54] METHOD OF DETERMINING A DENSITY DISTRIBUTION OF POSITRONS IN HUMAN TISSUE

[75] Inventors: Jakob Schelten, Jülich; Richard Reinartz, Langerwehe, both of Fed. Rep. of Germany

[73] Assignee: Forschungsentrum Julich GmbH, Julich, Fed. Rep. of Germany

[21] Appl. No.: 963,577

[22] Filed: Oct. 19, 1992

[30] Foreign Application Priority Data

Oct. 18, 1991 [DE] Fed. Rep. of Germany ....... 4134435

[51] Int. Cl.$^5$ .............................................. G01T 1/172
[52] U.S. Cl. ................................ 250/394; 250/363.04; 364/413.13
[58] Field of Search .............. 250/363.03, 394, 363.07; 364/413.01, 413.13

[56] References Cited

U.S. PATENT DOCUMENTS

| | | | |
|---|---|---|---|
| 4,057,727 | 11/1977 | Muehllehner et al. | 250/363.03 |
| 4,151,416 | 4/1979 | Richey et al. | 250/363.07 |
| 4,566,074 | 1/1986 | Nishikawa | 364/571.04 |
| 4,755,679 | 7/1988 | Wong | 250/363.03 |
| 4,789,933 | 12/1988 | Chen et al. | 364/413.13 |
| 4,931,968 | 6/1990 | Hirose | 364/571.02 |

FOREIGN PATENT DOCUMENTS 63-83687  4/1988  Japan ............................ 364/413.13

*Primary Examiner*—Constantine Hannaher
*Attorney, Agent, or Firm*—Herbert Dubno

[57] ABSTRACT

A process for determining the density distribution of positrons in human tissue in which the amount of position data stored in the computer memory from two parallel photomultiplier local position γ-detectors is limited by a random-event generator connected to the computer.

6 Claims, 3 Drawing Sheets

METHOD OF DETERMINING A DENSITY DISTRIBUTION OF POSITRONS IN HUMAN TISSUE

FIELD OF THE INVENTION

Our present invention relates to a method of determining the density distribution of positrons decaying in human tissue and to a device or apparatus for determining the density distribution of such positrons in human tissue.

BACKGROUND OF THE INVENTION

Positrons decaying in human tissue give rise to two oppositely travelling γ-quanta which can be detected by two γ-detectors disposed opposite one another across the human tissue and flanking the body portion examined.

The γ-detectors are generally connected to a computer which, upon coincidence of the detection of two γ-quanta from signals of the opposing γ-detectors, can register a given positron decay. The computer can calculate the flight paths of the two γ-quanta arising from the same positron decay and thus generate position information as to the decaying positron.

The position information can be stored in the computer and the positions of the γ-detectors varied so that, from the sum total of the position information obtained, a distribution function of the positron decays can be generated and the computer can, from the distribution function, generate a density distribution of the positron decay which represents information relating to the tissue.

This process is referred to as positron emission tomography (PET) and is increasingly being employed for medical evaluations and in scientific research as to human tissues, pathological conditions and the like.

A patient is injected with or inhales a radio-pharmaceutical with a positron emitting isotope and the localization of the positrons in the human organism can be detected by the PET. In human tissue, the emitted positrons have a range of millimeters to several centimeters depending upon their energies which are typically between 1 and 5 MeV, and decay when they come to rest in the aforementioned manner.

In the present day PET scanners, individual detectors are assembled in opposing detector banks and are capable of detecting only a small part of the emitted radiation. It is thus required to rotate the detector assemblies around the object to be measured and to shift the detector assembly vertically to be able to cover a relatively large space angle in a sequence of measurements. This requires a relatively long measuring period for the process which an result in an undesirably long exposure of the human organism to radiation and thus an undesirably large radiation load on the patient.

Apart from such individual detectors, γ-quanta can be measured by local resolution photomultipliers having scintillators ahead of photomultiplier tubes and at the exposure window. These devices can provide a detector surface with diameters of 10 cm and can achieve a local resolution of 1 mm.

Typically $10^8$ decay events can be detected in the course of a single measurement process to determine density distribution of the positron decay events. By the use of such photomultipliers instead of individual detectors, the detection of $10^8$ decays can be substantially accelerated and thus the period of measurement can be reduced by an order of magnitude. However, this usually requires 16 angular positions of the photomultipliers around the subject and four vertical positions so that the memory for the resulting data must be at least 425 MB (megabytes) to afford the data search required to provide the desired information as to the density distribution.

The computers usually used for positron emission tomography, however, generally are incapable of processing this substantial data flow from the photomultipliers in an on-line mode, nor do they have such high data storage capacities.

OBJECTS OF THE INVENTION

It is, therefore, the principal object of the present invention to provide a method of and an apparatus for determining a density distribution of positrons decaying in human tissue whereby these drawbacks are avoided.

A more specific object of the invention is to reduce the measuring period in PET to limit the radiation loading of the subject or patient without significantly increasing the capital cost of positron emission tomography equipment.

It is also an object of this invention to provide a system for effecting positron emission tomography with minimum radiation loading of the subject but with high resolution and accuracy of determination of the density distribution of the positron decay.

SUMMARY OF THE INVENTION

These objects and others which will become apparent hereinafter are attained, in accordance with the invention, by providing parallel-oriented opposing γ-detectors in the form of local resolution photomultipliers and storing in the computer only a portion of the outputted data as determined by instances selected by a random event generator, this portion of the position information being selected to be the maximum permitted for on-line data storage without exceeding the capacity of the computer.

The method according to the invention thus comprises the steps of:

(a) disposing on two opposite sides of human tissue in which a positron density distribution is to be determined a pair of γ-detectors in the form of mutually parallel locally resolving photomultipliers outputting respective signals upon detection of respective γ-quanta;

(b) with a computer connected to the γ-detectors, registering each event corresponding to simultaneous detection of two γ-quanta deriving from decay of the same positron in the tissue;

(c) computing with the computer upon each registration of two γ-quanta deriving from decay of the same positron in the tissue the paths of the respective γ-quanta, thereby determining a location of the corresponding positron in the tissue, and storing information as to the location in the computer in a memory only at instances selected by a random-event generator;

(d) varying positions of the γ-detectors relative to the tissue and repeating steps (a) to (d) to accumulate in the computer information as to a multiplicity of the locations of positron decay, and automatically generating a distribution function of the locations;

(e) selecting the number of locations stored in response to the random-event generator to be a maximum permitted for on-line data storage without exceeding a capacity of the computer; and (f) calculating from the distribution function a density distribution of the positrons in the tissue.

To minimize information loss, for each calculated flight path which is to produce position information selected by the random-event generator, a coordinate of this flight path, here referred to as an event coordinate, is arbitrarily selected, the allowable random-event generator count being so limited that these event coordinates which are stored are those which are in the vicinity of the human tissue or are therein.

A simple and rapid storage can be effected of the event coordinates where space is subdivided into individual space elements and each of said space elements is assigned a memory-location address, an event coordinate in one of said space elements being stored by incrementing by one the corresponding memory location, thereby obtaining a event coordinate distribution $B_i$, a resolution $A_{ik}$ being determined experimentally, by computer simulation, or by analytical approximation, and the density distribution $E_k$ of the decaying positrons being determined from:

$$\Sigma_k A_{ik} E_k = B_i$$

The event-coordinate distribution is thus obtained from the individual positron irradiators instead of from the patient between the photomultipliers.

The evaluation of the event-coordinate distribution can be effected, for example, by calculating the density distribution of the decaying positrons $E_k$ iteratively according to:

$$y_k^{(n+1)} = a \cdot y_k^{(n)} \cdot \left( \frac{B_k}{\sum_j A_{kj} \cdot y_j^{(n)}} \right)^\eta$$

$$0.1 < \eta < 10$$

beginning with $$y_k^{(0)} = \frac{|B_k|}{\left| \sum_j A_{kj} \cdot B_j \right|} B_k.$$

is calculated.

An acceleration of this evaluation can be achieved by approximating the sum $$S_k = \sum_j A_{kj} \cdot y_j^{(n)}$$

in a summation over the diagonal elements and by averaging over the remaining elements, i.e.

$$S_k = \sum_{|j-k| \leq m} A_{kj} y_j^{(n)} + \sum_{|j-k| > m} (A_k) y_j^{(n)}$$

whereby $$(A_k) = \frac{\sum_{|j-k|>m} A_{kj}}{\sum_{|j-k|>m} 1}.$$

The process of the invention can be carried out with an apparatus in which the local resolving photomultipliers forming the γ-detectors are parallel to one another and the computer is provided with or connected to a random-event generator which selects the data transmitted randomly but only at a rate allowing the on-line data storage without exceeding the computer capacity so that only a portion of the position information is storageable in the memory on an on-line basis. In the following example, a simulation of the process is described.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
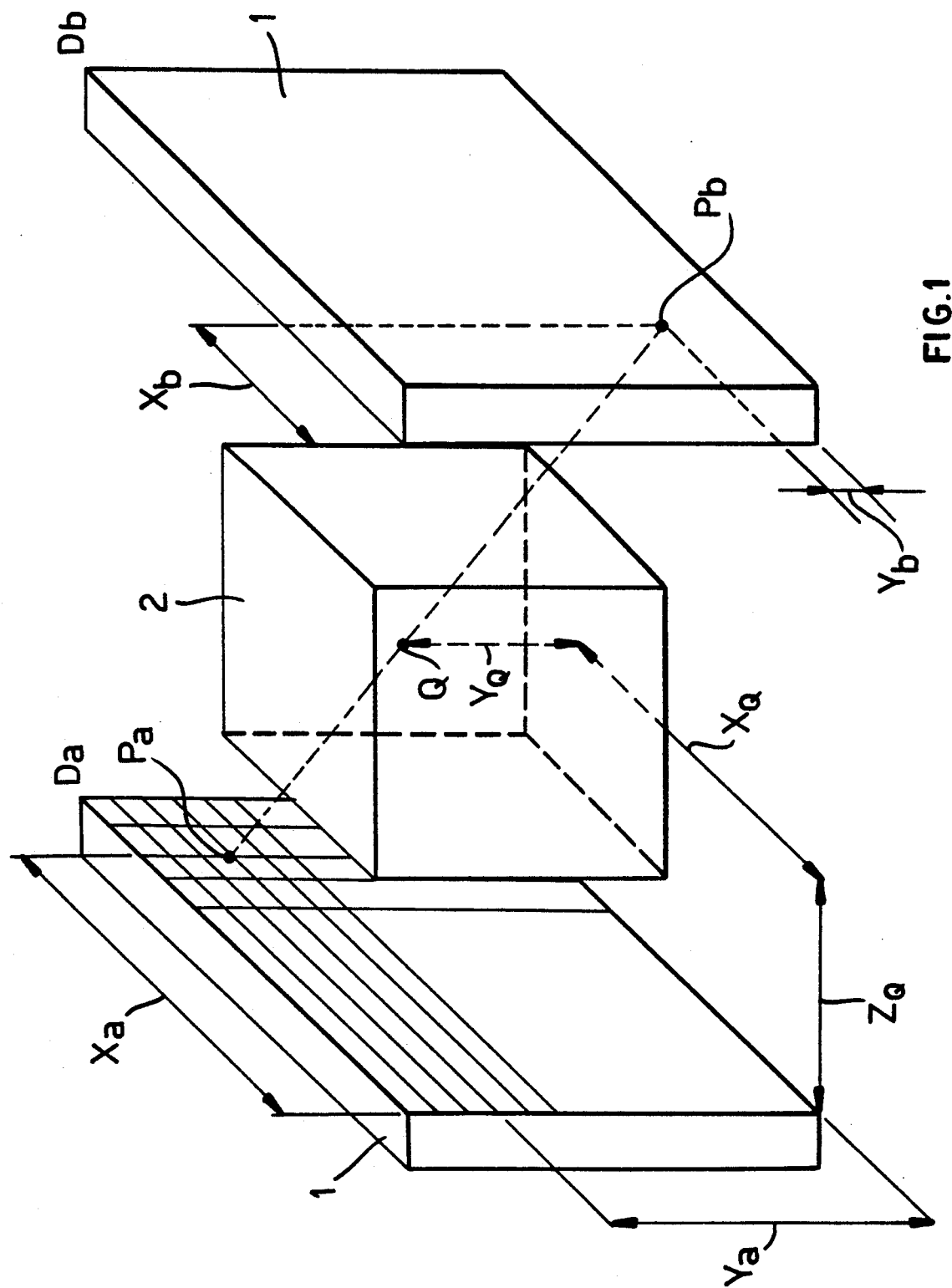
FIG. 1 is a diagram illustrating how the measurements are effected with two local resolution photomultipliers which are provided to flank an object to be subjected to measurement and having the shape of a cube.
Figure 2:
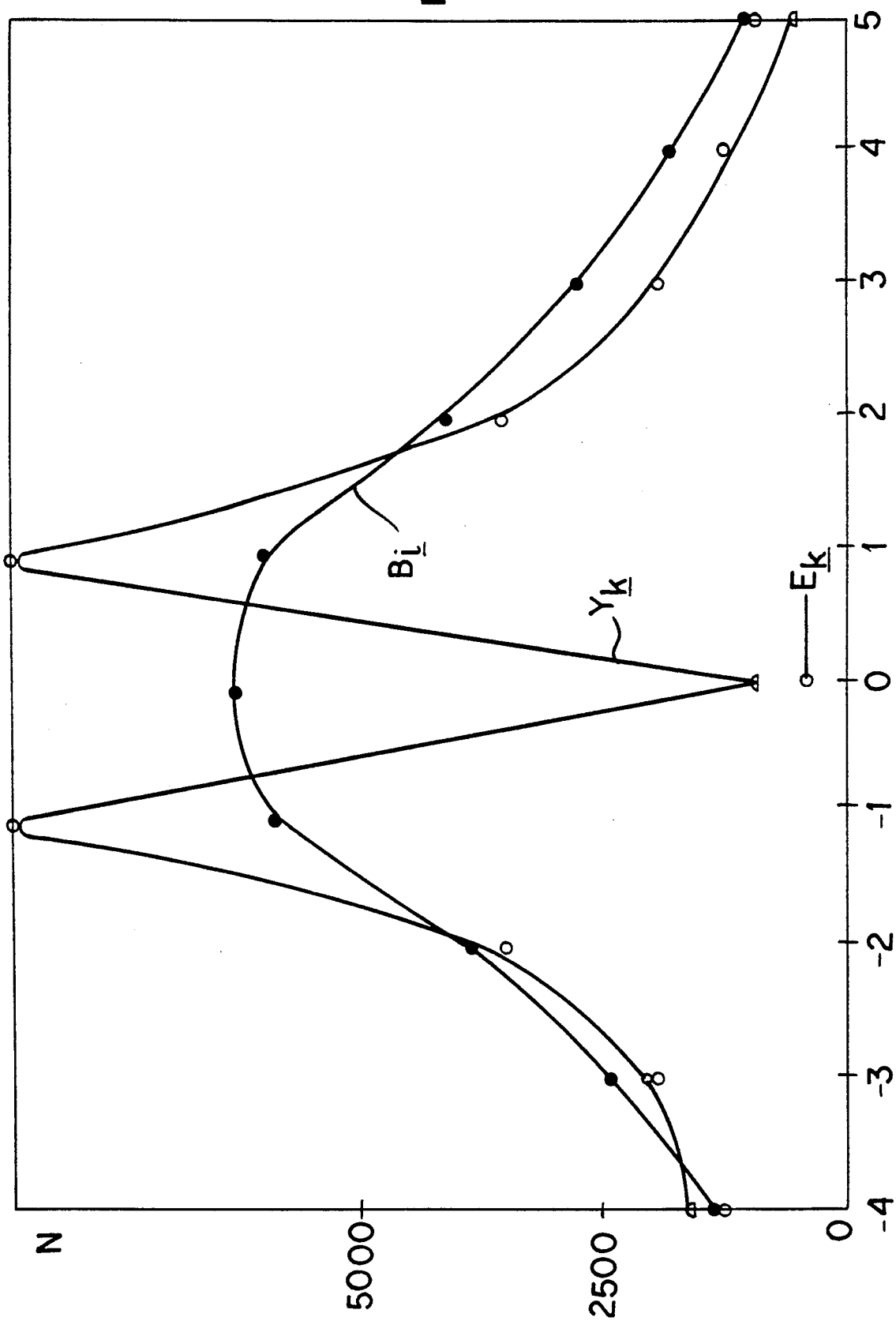
FIG. 2 is a graph illustrating the invention.

FIG. 1 shows a pair of local resolution photomultipliers $D_a$ and $D_b$ which are parallel to one another on opposite sides of the object which is here in the form of a cube. In FIG. 2, the measured value $B_i$, resulting from the decay $E_k$ has been illustrated together with the calculated result $Y_k$.

EXAMPLE

The simulation experiment is based upon the following initial situation.

Figure 3:
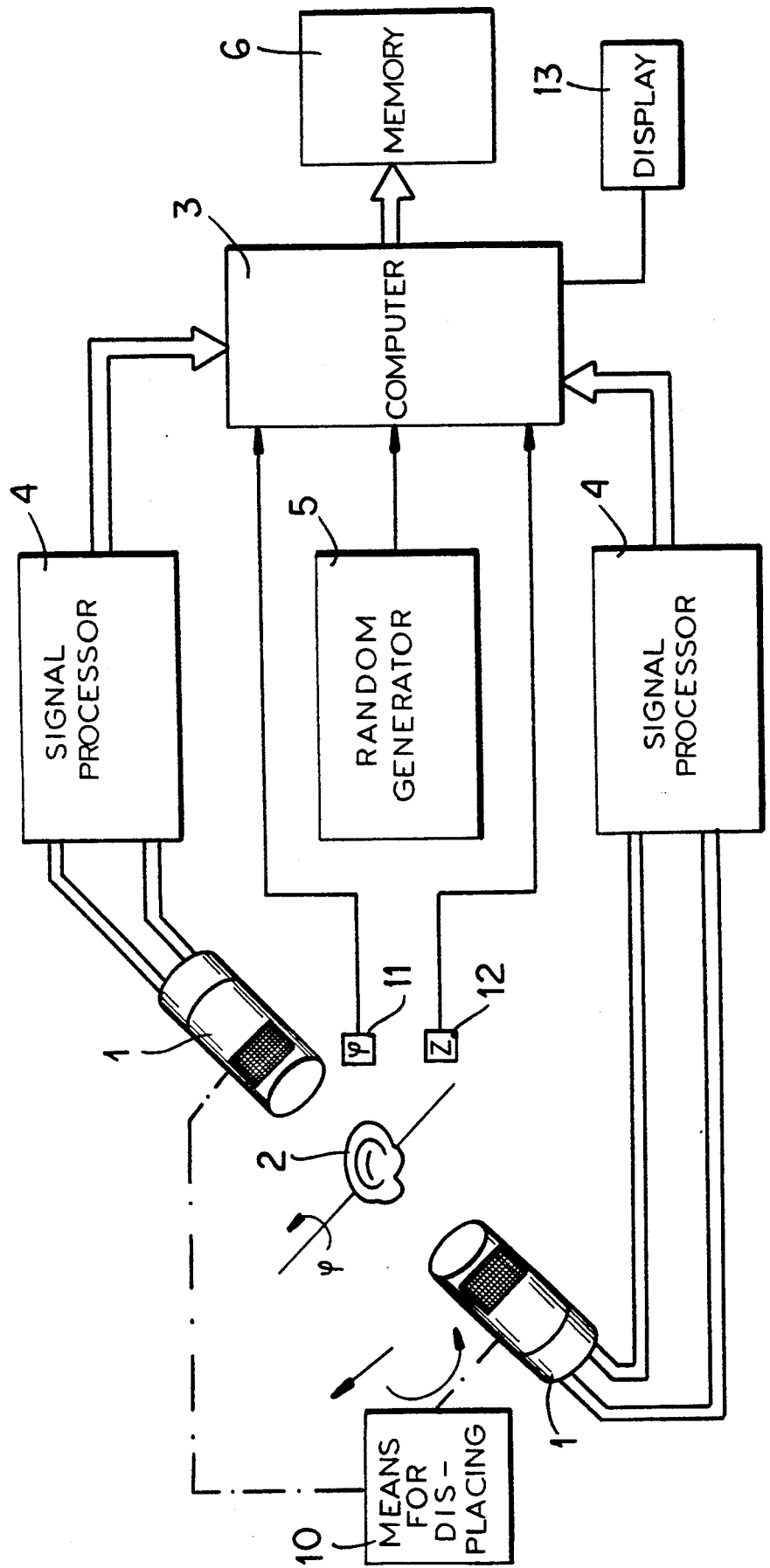
FIG. 3 is a block diagram of an apparatus for carrying out the invention.

A human body part 2 is disposed between a pair of locally resolving photomultipliers 1 shown in their parallel relation in FIG. 1 and more diagrammatically in FIG. 3. If a position decay occurs at point Q (FIG. 1), it produces two γ-quanta in opposite directions impinging at points $P_a$ and $P_b$ at the detectors $D_a$ and $D_b$. The locations of this impingement at the detectors are determined by the coordinates $(X_a, Y_a)$ and $(X_b, Y_b)$, producing corresponding output signals so that the computer, which receives a passing signal from a random-event generator 5 with a count r where $r_a < r < r_b$ and $$X_Q = (1-r) \cdot X_a + r \cdot X_b$$

$$Y_Q = (1-r) \cdot Y_a + r \cdot Y_b$$

$$Z_Q = (1-r) \cdot Z_a + r \cdot Z_b$$

where the event coordinate is $(X_Q, Y_Q, Z_Q)$.

If desired, these coordinates can be transformed into a space fixed coordinate system. $r_a$ and $r_b$ are constants so selected that the event coordinates lie in or close to the human tissue.

The body part examined can be subdivided into a predetermined number of unit volume elements (indicated by the coefficient triple $i = (i_1, i_2, i_3)$. Each unit volume element in which the event coordinate may lie addresses a memory location in the computer. By incrementing these memory locations, each such positron decay event is recorded. By accumulating the events, the blurred event density distribution $B_i$ is obtained.

In positron emission tomography, the computers carry out the required calculation steps in an on-line mode as long as the count rate does not substantially exceed $10^5$ per second.

If the human body part is subdivided into 1000 unit volume elements and the positron decay events are detected over a space angle between the detectors 1 and the element 2 by rotation of the detectors around the Y axis or vertical displacement along the Y axis, the measurement curve $B_i$ shown in FIG. 2 is obtained.

The resolution vector $E_k$ is calculated from the relationship $$\sum_k A_{ik} \cdot E_k = B_i$$

from the blurred event density distribution. The resolution matrix $A_{ik}$ is thus the accumulated event density when all decays occur at a single point Q.

$A_{ik}$ in the present simulation experiment is calculated analytically.

The desired function $E_k$ is determined from the measured values $B_i$ in accordance with the following considerations:

The components of the $n+1$ vector $Y^{(n+1)}$ are calculated componentwise from the n-th vector $Y^{(n)}$ according to $$y_k^{(n+1)} = \alpha \cdot y_k^{(n)} \cdot \left( \frac{B_k}{\sum_j A_{kj} \cdot y_j^{(n)}} \right)^{\eta}$$

$$0.1 < \eta < 10$$

whereby initially $\alpha$ is said to equal 1. The sequence begins with the vector $$y_k^{(l)} = \frac{|B_k|}{\left| \sum_j A_{kj} \cdot B_j \right|} B_k.$$

In these relationships the $|\ |$ represents the Euclidic vector standard, i.e.

$$|B_k| = \left( \sum_k B_k^2 \right)^{\frac{1}{2}}.$$

The sum $$S_k = \sum_j A_{kj} \cdot y_j^{(n)}$$

Q is broken down approximately into the sum over the diagonal elements and the average value of the remaining elements, i.e.

$$S_k = \sum_{|j-k| \leq m} A_{kj} y_j^{(n)} + \sum_{|j-k| > m} (A_k) y_j^{(n)}$$

where $$(A_k) = \frac{\sum_{|j-k|>m} A_{kj}}{\sum_{|j-k|>m} 1}.$$

and $m = 3$.

This iteration process is interrupted since, for the $n+1$ solution vector, the divergence is $$\left| \sum_k A_{ik} \cdot y_k^{(n+1)} - B_i \right| \leq \epsilon \cdot |B_i|$$

Depending upon the exponent, the number of iterations will be affected.

The normalization factor $\alpha$ is so selected that for the normalization of the vectors $$\left| \sum_k A_{ik} \cdot y_k^{(n+1)} \right| = |B_i|$$

applies.

Between 20 and 50 iteration steps are required to reach the limit $\epsilon = 1 \times 10^{-4}$.

In FIG. 2, the so calculated solution vector $Y_k$ is illustrated. The relative deviation from the selected solution vector is of the order of magnitude $10^{-3}$.

Referring now to FIG. 3, it can be seen that the photomultipliers 1 are arranged parallel to one another but are associated with the means 10 for displacing them about and along the Y axis so that the photomultipliers together can be rotated around object 2 through an angle $\phi$ and can be shifted by a displacement Z. Sensors 11 and 12 for the angular displacement and the linear displacement provide outputs to the computer 3 as well.

The signal processors 4 supply the computer with the signals from the photomultipliers 1. The computer 3 affects a coincidence determination for the signals from the photomultipliers and calculates the flight paths so that the position information with respect to the positron decay can be stored in the memory 6 of the computer. The stored information, limited in quantity because of the storage and response to the random-event generator 5, following the measurement process, is evaluated by the computer in the manner described to yield the positron decay density information which can be displayed at 13 in accordance with conventional PET techniques.

We claim:

1. A method of determining a density distribution of positrons decaying in human tissue into two oppositely traveling γ-quanta, comprising:

(a) disposing on two opposite sides of human tissue in which a positron density distribution is to be determined a pair of γ-detectors in the form of mutually parallel locally resolving photomultipliers outputting respective signals upon detection of respective γ-quanta;

(b) with a computer connected to said γ-detectors, registering each event corresponding to simultaneous detection of two γ-quanta deriving from decay of the same positron in said tissue;

(c) computing with said computer upon each registration of two γ-quanta deriving from decay of the same positron in said tissue the paths of the respective γ-quanta, thereby determining a location of the corresponding positron in the tissue, and storing information as to said location in said computer in a memory only at instances selected by a random-event generator;

(d) varying positions of said γ-detectors relative to said tissue and repeating steps (a) to (d) to accumulate in said computer information as to a multiplicity of said locations of positron decay, and automatically generating a distribution function of said locations;

(e) selecting the number of locations stored in response to said random-event generator to be a maximum permitted for on-line data storage without exceeding a capacity of said computer; and (f) calculating from said distribution function a density distribution of said positrons in said tissue.

2. The method defined in claim 1 wherein for each of the γ-quanta paths computed with said computer a coordinate of the path, denominated an event coordinate, is arbitrarily selected and the information permitted to be stored by said random-event generator includes only said event coordinates at or proximal to said tissue.

3. The method defined in claim 2 wherein an event coordinate space is subdivided into individual space elements and each of said space elements is assigned a memory-location address, an event coordinate in one of said space elements being stored by incrementing by one the corresponding memory location, thereby obtaining a event coordinate distribution $B_i$, a resolution $A_{ik}$ being determined experimentally, by computer simulation, or by analytical approximation, and the density distribution Ek of the decaying positrons being determined from:

$$\Sigma_k A_{ik} \cdot E_k = B_i.$$

4. The method defined in claim 3 wherein the density distribution of the decaying positrons Ek is determined iteratively by:

$$y_k^{(n+1)} = a \cdot y_k^{(n)} \cdot \left( \frac{B_k}{\sum_j A_{kj} \cdot y_j^{(n)}} \right)^\eta$$

$$0.1 < \eta < 10$$

beginning with $$y_k^{(l)} = \frac{|B_k|}{\left| \sum_j A_{kj} \cdot B_j \right|} B_k.$$

5. The method defined in claim 4 wherein in the iterative density distribution a sum is formed in accordance with the relation $$S_k = \sum_j A_{kj} \cdot y_j^{(n)}$$

approximated by a summation over the diagonal elements and the formation of an average value over the remaining elements according to $$S_k = \sum_{|j-k| \leq m} A_{kj} y_j^{(n)} + \sum_{|j-k| > m} (A_k) y_j^{(n)}$$

where $$(A_k) = \frac{\sum_{|j-k|>m} A_{kj}}{\sum_{|j-k|>m} 1}.$$

6. An apparatus for determining a density distribution of positrons decaying in human tissue into two oppositely traveling γ-quanta, said apparatus comprising:

a pair of γ-detectors in the form of mutually parallel locally resolving photomultipliers outputting respective signals upon detection of respective γ-quanta and disposed on two opposite sides of human tissue in which a positron density distribution is to be determined;

a computer connected to said γ-detectors, registering each event corresponding to simultaneous detection of two γ-quanta deriving from decay of the same positron in said tissue;

means in said computer upon each registration of two γ-quanta deriving from decay of the same positron in said tissue for calculating the paths of the respective γ-quanta, thereby determining a location of the corresponding positron in the tissue;

a random-event generator connected to said computer;

means for storing information as to said location in said computer in a memory only at instances selected by said random-event generator;

means for varying positions of said γ-detectors relative to said tissue to accumulate in said computer information as to a multiplicity of said locations of positron decay, and automatically generating a distribution function of said locations, the number of locations stored in response to said random-event generator being a maximum permitted for on-line data storage without exceeding a capacity of said computer, said computer calculating from said distribution function a density distribution of said positrons in said tissue.

* * * * *